United States Patent [19]

Freier

[11] 4,217,899
[45] Aug. 19, 1980

[54] COLONIC ENDOPROSTHESIS

[76] Inventor: Lutz Freier, Hausserstr. 140, 7400 Tübingen 1, Fed. Rep. of Germany

[21] Appl. No.: 847,820

[22] Filed: Nov. 2, 1977

[51] Int. Cl.$^2$ ............................................. A61F 5/44
[52] U.S. Cl. ................................ 128/283; 128/1 R; 128/275; 128/DIG. 25
[58] Field of Search ............... 128/283, 275, DIG. 25, 128/1 R, DIG. 23, 285; 220/410, 408, 409, 411

[56] References Cited

U.S. PATENT DOCUMENTS

| 688,517 | 12/1901 | Held | 220/408 X |
|---|---|---|---|
| 2,324,520 | 7/1943 | Lamson | 128/DIG. 25 |
| 2,452,813 | 11/1948 | Wade | 128/275 |
| 2,943,625 | 7/1960 | Lotts | 128/275 X |
| 3,216,420 | 11/1965 | Smith et al. | 128/283 |
| 3,275,180 | 9/1966 | Optner et al. | 220/411 X |
| 3,802,418 | 4/1974 | Clayton | 128/283 |
| 3,828,782 | 8/1974 | Polin | 128/283 |

OTHER PUBLICATIONS

Webster's Seventh New Collegiate Dictionary, G. C. Merviam Co., Springfield, Mass., "Container", p. 180.

Primary Examiner—Robert W. Michell
Assistant Examiner—J. Kruter
Attorney, Agent, or Firm—Michael J. Striker

[57] ABSTRACT

A colonic endoprosthesis includes a tubular jacket element which consists of two tubular members which are telescopically received within one another and arrested in a telescoped position thereof when the tubular jacket element is implanted in the body of a user. A container element consisting of a hollow support member and an elastic lining member received in the hollow support member is removably insertable into the jacket element and retained in the fully inserted position thereof. The distal end of the intestinal tract of a user is connected to and communicates with the colonic endoprosthesis for the digested matter to enter and accummulate in the elastic lining member mounted on the support member of the container element until the time for emptying the hollow support member. Both the jacket element and the container element may be straight, or they may assume an S-shaped configuration when implanted and inserted so as to conform to the natural course of the original distal end of the intestinal track of the user. A connecting frame mounts the implanted jacket element in the pelvic basin of the user so that a distal end of the jacket element is situated at the location of the original anal sphincter.

17 Claims, 5 Drawing Figures

COLONIC ENDOPROSTHESIS

BACKGROUND OF THE INVENTION

The present invention is related to an endoprosthesis to be implanted in the body of a user as a substitute for a removed portion of a tract of the user in general, and more particularly to an endoprosthesis which substitutes for the distal end of the digestive track of the user portions of whose small or large intestine have been operatively removed.

It is well known that, in connection with some ailments, such as intestinal cancer, it is sometimes necessary to remove portions of the digestive tract of a patient, such as portions of the small intestine or portions of the large intestine. Under these circumstances, it is sometimes necessary to also remove the rectal portion of the colon, including the anal sphincter. Thus, alternate means must be found for the removal of the feces from the body of the user.

One of the techniques which have been heretofore used to solve this problem was to give the patient whose intestinal parts or rectum had to be removed an abdominal substitute rectum. An article entitled "Komplikationen der Ileostomie und Colostomie und ihre Behandlung" (Complications of the Ileostomy and Colostomy and their Treatment), appearing in the magazine "Der Chirurg", Vol. 47 (1976), No. 1, pp. 16 to 21 discusses the psychological problems for the patient and the encountered complications when this operative procedure is resorted to. In this connection, it is to be mentioned that the ileostomy or the colostomy do not involve the use of a colonic endoprosthesis; rather, they involve an opening of the frontal abdominal wall, and the connection of the distal end of either the large intestine or the small intestine to the frontal abdominal wall at such an opening.

A continent ileostomy has been introduced by N. G. Kock in the passage entitled "Continent Ileostomy" appearing in "Progress in Surgery", vol. 12, pp. 180 to 201, published by Karger-Verlag in Basel in 1973. This publication describes the formation of a reservoir from a portion of a small intestine which aids in the discharge of the digested matter from the body of the user. This reservoir is arranged upstream of the per se unnatural substitute rectum which opens onto the abdominal wall. Even here, the solution does not involve any colonic endoprosthesis inasmuch as, first of all, the reservoir is formed from a natural tissue of the body of the user and, secondly, it does not take the place of the colon so that it neither replaces, nor permits the removal of, the abdominal rectum.

Even the "Kontinente Kolostomie durch Magnetverschluss" (Continent colostomy by a Magnetic Closure) disclosed by Feustel and Hennig in the "Deutschen Medizinischen Wochenschrift" (German Medical Weekly), No. 100, May 1975, pp. 1063 and 1064, does not involve the use of a colonic endoprosthesis; rather, it reveals a particularly progressive kind of the closure for an otherwise known abdominal rectum. According to this publication, a magnetic ring is implanted under the skin or under the mucous membrane at the abdominal wall, and a permanently magnetic lid having a centrally located plug closes the discharge opening in the abdominal wall due to the magnetic attraction between the lid and the implanted magnetic ring. Even here, no colonic endoprosthesis is involved inasmuch as there is provided only a closure of an abdominal rectum by resorting to new technical means, and no special reservoir for the accommodation of the digested matter is used in this arrangement.

All of the above-discussed operative and post-operative procedures are disadvantageous in that they subject the patients to a considerable mental stress of the presence, appearance and handling of an artifical rectum located at the front abdominal wall. Heretofore, no viable alternative to this unpleasant and often excruciating experience has been available.

SUMMARY OF THE INVENTION

Accordingly, it is a general object of the present invention to avoid the disadvantages of the prior art.

More particularly, it is an object of the present invention to find an alternative to the above-discussed techniques which does not subject the patient whose part of the intestinal tract had to be operatively removed to the mental anguish associated with the heretofore-used techniques.

It is a concomitant object of the present invention to provide a colonic endoprosthesis which enables the patient to discharge the digested matter from a natural part of the body.

A further object of the present invention is to provide a colonic endoprosthesis which is simple in construction, inexpensive, reliable in operation, and relatively convenient to use.

In pursuance of these objects, and others which will become apparent hereafter, one feature of the present invention resides, briefly stated, in a colonic endoprosthesis which comprises a tubular jacket element adapted to be implanted in the body, and to be connected to and communicate with the distal end of the intestinal tract, of a user; a container element removably insertable into the jacket element; and means for retaining the container element in a fully inserted position thereof relative to the jacket element. By resorting to the use of the colonic endoprosthesis of this type, there is obtained a situation in which the colonic endoprosthesis can take the place of the removed rectum and/or a portion of the sigmoid colon and in which the feces or only partially digested food are accommodated until the accumulated matter is removed from the body at the natural portion of the body of the user.

According to a currently preferred aspect of the present invention, the jacket element of the colonic endoprosthesis includes an outer tubular member, an inner tubular member telescopically received in the outer tubular member, and means for arresting the inner tubular member in a predetermined telescoped position relative to the outer tubular member. Then, the container element may include a hollow support member and an elastic lining member mounted on and received in the hollow support member. The jacket element may be elongated and rigid having a straight longitudinal axis. Then, the support member is also elongated, and advantageously rigid, and has a longitudinal axis which coincides with the axis of the jacket element in the fully inserted position of the container element. On the other hand, the implanted jacket element may be of a substantially S-shaped configuration to substantially conform to the natural course of the original distal end of the intestinal tract of the user, and then the container element will be elastically yieldable to conform to the shape of the jacket element in the fully inserted position of the jacket element. Advantageously, the jacket element is elastically yieldable for the implanted jacket element to assume the abovementioned S-shaped configuration.

The retaining means may include a threaded connection between the elements, or other complementary projections and recesses on the elements which engage one another at least in the fully inserted position.

According to a further advantageous aspect of the present invention, the colonic endoprosthesis further includes means for connecting the jacket element to the skeleton of the user, the connecting means preferably including a connecting frame, means for affixing the connecting frame to the skeleton, and means for mounting the jacket element on the connecting frame for adjustment of the relative position of the former with respect to the latter and for blocking the jacket element in a predetermined relative position thereof. The connecting frame has such a configuration as to be receivable in the pelvic basin of the user; then, the affixing and blocking means fixes the implanted jacket element in such a position that a distal end thereof is situated substantially at the location of the original anal sphincter.

The jacket element is connected to the distal end of the intestinal tract of the user and communicates therewith, advantageously by means of a tubular connecting element arranged at a proximal end of the implanted jacket element. Furthermore, the connecting means may include an inlet funnel communicating the distal end of the intestinal tract of the user with, and converging toward, the container element. Preferably, at least one projection is provided on a distal end of the container element by means of which the container element can be removed from the jacket element.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DISCUSSION OF THE PREFERRED EMBODIMENTS

Figure 1:
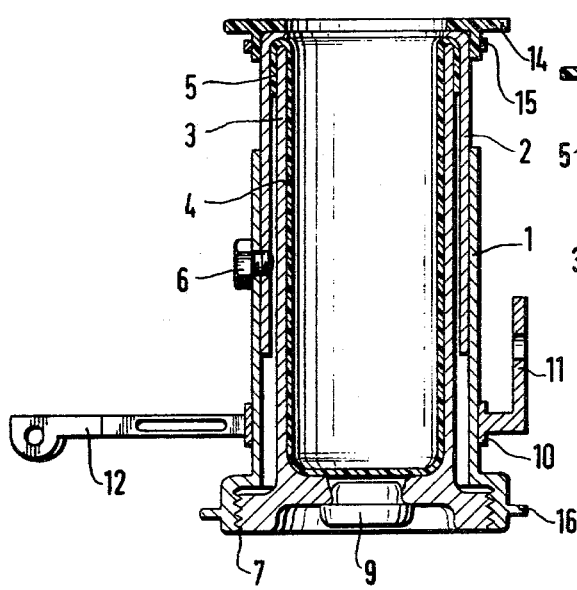
FIG. 1 is a longitudinal section of a straight colonic endoprosthesis of the present invention.

Referring now to the drawing in detail, and first to FIG. 1 thereof, it may be seen that the reference numeral 1 designates an outer jacket member and the reference numeral 2 identifies an inner jacket member, the members 1 and 2 together constituting a jacket element. A hollow support member 3 serves as a support for a bag-shaped lining member 4, for instance, of a synthetic plastic material, having an open end 5 which is folded around a rim of the support member 3. The support member 3 and the lining member 4 together constitute a container element which can be inserted into and retained in the interior of the jacket element 1, 2.

The jacket members 1 and 2 of the jacket element are telescopically received within one another and can be arrested in a selected position relative to each other by means, for instance, of a screw 6. However, it is to be understood that any other known and usable arresting arrangement can be employed, for instance, a resiliently yieldable tongue provided on one of the tubular members 1 and 2 and engaging one of a series of openings provided in the other of the members 2, 1.

Figure 1A:
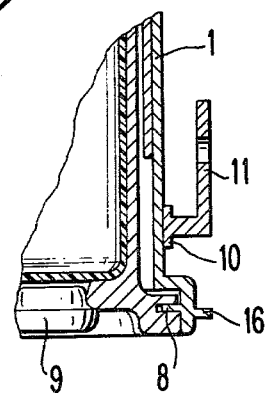
FIG. 1a is a portion of a longitudinal section of the straight colonic endoprosthesis shown in FIG. 1.

The support member 3 of the container element can be connected, for instance, to the outer jacket member 1, for example, as illustrated on the left-hand side of FIG. 1, by means of a threaded connection 7 or, as illustrated on the right-hand side of FIG. 1a, by means of a bayonet connection 8.

Advantageously, a bore is provided in the bottom of the support member 3, and a screw or a plug 9 is provided which closes the opening in the bottom of the support member 3. This opening becomes particularly useful when the patient is confined to bed with some ailment and suffers from diarrhea. Under these circumstances, the bag-shaped lining member 4 of synthetic plastic material can be perforated from the outside and the flowable fecal matter can be conducted away by a non-illustrated hose or the like.

A connecting frame 10 is mounted at the outside of the outer jacket member 1 for adjustment of the position relative to the latter. The connecting frame 10 has a bracket 11 which can be connected to the sacrum or to the coccyx, and two arms 12 which can be connected to the spinal ischiadicae or to the tubera ischiadica. The position of the connecting frame 10 on the jacket member 1, the inclination of the bracket 11 and the length or the direction of the arms 12 can be changed in order to adjust to the peculiar dimensions of each patient by adjustment of the position, bending or crossing.

The jacket members 1, 2, the connecting frame 10 and the container 3 can be made of hypoallergenic materials, for instance, metals such as an acid and corrosion resistant X 5CrNiMo 1810 steel. However, at least the support member 3 may be made of a synthetic plastic material, such as a duroplastic material. Cutouts 13 are provided at the bottom of the support member 3, which facilitates the turning of the support member 3 in engagement of the threads 7, or the manipulation of the support member 3 for engaging or disengaging the bayonet connection 8.

An annular connecting member 14, for example, of Dacron, is held at the upper or proximal end of the inner jacket member 2 by means of a hose-shaped shell 15. A lower end of the remaining intestine, ileum or sigmoid colon is connected to the connecting member 14, after radially extending the lower marginal portion of the distal end of the remaining intestine, in a known manner, such as by sewing, using, for instance, overcast stitches or other sewing techniques. A similar connecting member 16 can also be provided at the outer jacket member 1.

Figure 3:
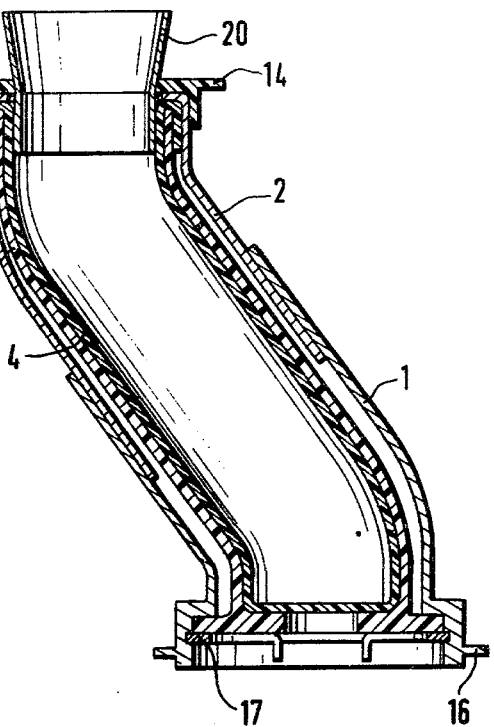
FIG. 3 is a view similar to FIG. 1 of a curved colonic endoprosthesis.
Figure 2:
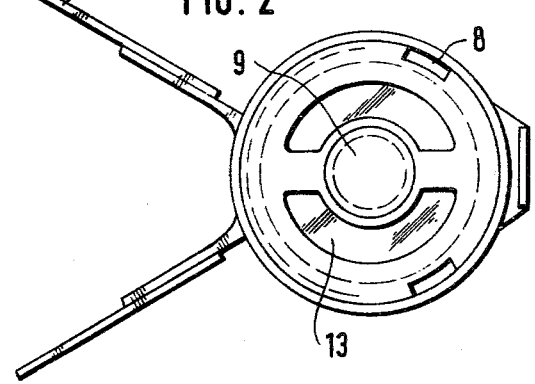
FIG. 2 is a bottom plan view of FIG. 1.
Figure 3A:
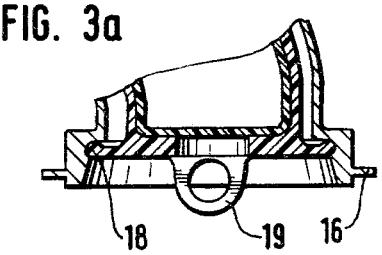
FIG. 3a is a fragmentary view illustrating a modified lower part of FIG. 3.

In the embodiment illustrated in FIG. 3, the colonic endoprosthesis is better accommodated to the shape of the depression of the sacrum in that it assumes an S-shaped configuration. As a result of this, the artificial rectum can be made longer and can be better adjusted to the natural circumstances and conditions prevailing inside the abdominal cavity of the user. The parts of the colonic endoprosthesis which have the same function as the corresponding parts of the embodiment of FIG. 1 have been given the same reference numerals. A flexible synthetic plastic material is being used, under these circumstances, as the material at least for the support member 3. When it is desired to reinforce the support member 3 while keeping it flexible, a metallic insert may be embedded in or otherwise connected to the support member 3, and may have a helical configuration. In view of the fact that, when the support member 3 is to have, at least in its fully inserted position, an arcuate configuration conforming to the configuration of the jacket members 1, 2, a threading-in of the support member 3 into the jacket members 1, 2 may be very difficult, if not impossible, there are illustrated other types of retention of the support member 3 in its fully inserted position which can be used instead of the above-discussed threaded connection 7, or bayonet connection 8. So, for instance, the reference numeral 17 identifies an open resiliently yieldable retaining ring which possesses outwardly bent actuating end portions. Finally, the support member 3 of the container element may be provided with an annular bulge 18 (see FIG. 3a) which engages in a corresponding depression of the jacket member 1 with snap action or the like. In order to be able to easily extract the support member 3 together with the lining member 4 out of the channel of the jacket members 1, 2, the support member 3 may be provided with a yieldable or tiltable tab 19.

A funnel 20 (see FIG. 3) can be provided at the upper or proximal end of the colonic endoprosthesis, the upper end of the downwardly converging funnel 20 abutting against the inside of the mucous membrane of the sigmoid colon or other part of the intestine. The provision of this funnel improves the protection of the connection between the end of the intestine and the connecting member 14 from feces or other depositions.

It will be understood that each of the elements described above, or two or more together, may also find a useful application in other types of constructions differing from the types described above.

While the invention has been illustrated and described as embodied in a colonic endoprosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A colonic endoprosthesis comprising an elongated tubular jacket element adapted to be planted in the body of the user and having one end portion and another end portion spaced from said one end portion; a container element removably insertable into said jacket element so as to be located in the body of the user, said container element including a hollow support member and an elastic lining member mounted on and received in said hollow support member; means for retaining said container element in a fully inserted position thereof relative to said jacket element; a first connecting formation on said one end portion of said jacket element for connecting the latter to the distal end of the intestenal tract of the user; and a second connecting formation on said other end portion of said jacket element for connecting the same to the skin of the user so that feces or partially digested food are removed from the body through the colonic endoprosthesis.

2. A colonic endoprosthesis as defined in claim 1, wherein said jacket element includes an outer tubular member, an inner tubular member telescopically received in said outer tubular member, and means for arresting said inner tubular member in a predetermined telescoped position relative to said outer tubular member.

3. A colonic endorpsothesis as defined in claim 2, wherein said first connecting formation further includes an inlet funnel communicating the distal end of the intestinal tract of the user with, and converging toward said container element, said funnel being separate from said outer tubular member and preventing feces from entering between said inner and outer tubular members.

4. A colonic endoprosthesis as defined in claim 1, wherein said jacket element is elongated and rigid.

5. A colonic endoprosthesis as defined in claim 4, wherein said jacket element has a straight longitudinal axis; and wherein said support member is also elongated and has a longitudinal axis which coincides with said axis of said jacket element in said fully inserted position.

6. A colonic endoprosthesis as defined in claim 5, wherein said support member is rigid.

7. A colonic endoprosthesis as defined in claim 1, wherein said jacket element is elastically yieldable for the implanted jacket element to assume said S-shaped configuration.

8. A colonic endoprosthesis as defined in claim 1, wherein said retaining means includes a threaded connection between said elements.

9. A colonic endoprosthesis as defined in claim 1, wherein said retaining means includes complementary projections and recesses on said elements which engage one another at least in said fully inserted position.

10. A colonic endoprosthesis as defined in claim 1, and further comprising means for removing said container element from said jacket element, including at least one projection on a distal end of said container element.

11. A colonic endoprosthesis as defined in claim 1; and further comprising a container element removably insertable into said jacket element.

12. A colonic endoprosthesis as defined in claim 1, wherein said container has two opposite open ends, and means for detachably closing one open end of said container.

13. A colonic endoprosthesis as defined in claim 12, wherein said closing means include a plug readily removable from said one end of said container to thereby permit access to the interior of the container from the outside thereof.

14. A colonic endoprosthesis as defined in claim 1, wherein said first connecting formation includes an annular flange arranged at said one end portion of said jacket element.

15. A colonic endoprosthesis, comprising a tubular jacket element adapted to be implanted in the body and to be connected to and communicate with the distal end of the intestinal tract of a user, said pocket element being of a substantially S-shaped configuration to substantially conform to the natural course of the original distal end of the intestinal tract of the user; a container element removably insertable into said jacket element, and being elastically yieldable to conform to the shape of said jacket element in a fully inserted position thereof relative to said jacket element; and means for retaining said container element in said fully inserted position thereof.

16. A colonic endoprosthesis, comprising a tubular jacket element adapted to be implanted in the body, and to be connected to and communicate with the distal end of the intestinal tract, of a user; a container element removably insertable into said jacket element; means for retaining said container element in a fully inserted position thereof relative to said jacket element; and means for connecting said jacket element to the skeleton of the user, including a connecting frame, means for affixing said connecting frame to the skeleton, and means for mounting said jacket on said connecting frame for adjustment of the relative position of the former with respect to the latter and for blocking said jacket element in a predetermined relative position thereof.

17. A colonic endoprosthesis as defined in claim 16, wherein said connecting frame has such a configuration as to be receivable in the pelvic basin of the user; and wherein said affixing and blocking means fixes the implanted jacket element in such a position that a distal end thereof is situated substantially at the location of the original anal sphincter.

* * * * *